United States Patent [19]
Yetman et al.

[11] Patent Number: 5,164,066
[45] Date of Patent: Nov. 17, 1992

[54] ELECTROPHORESIS CASSETTE SYSTEM WITH APPARATUS AND METHOD FOR FILLING SAME

[75] Inventors: David S. Yetman, Merrimack; Philip C. Danby, Chestnut Hill, both of Mass.

[73] Assignee: EG&G Inc., Wellesley, Mass.

[21] Appl. No.: 394,760

[22] Filed: Aug. 16, 1989

Related U.S. Application Data

[63] Continuation-in-part of Ser. No. 127,655, Dec. 2, 1987, Pat. No. 4,929,329, which is a continuation-in-part of Ser. No. 43,212, Apr. 27, 1987, abandoned.

[51] Int. Cl.$^5$ .................... G01N 27/26; B01D 57/02
[52] U.S. Cl. .................... 204/299 R; 204/182.8
[58] Field of Search .................... 204/299 R, 182.8

[56] References Cited

U.S. PATENT DOCUMENTS

4,431,506 2/1984 Gorman Jr., et al. ........ 204/182.8 X
4,668,362 5/1987 November et al. .

*Primary Examiner*—John Niebling
*Assistant Examiner*—John S. Starsiak Jr.

[57] ABSTRACT

Apparatus for filling an electrophoresis cassette of the type having a gel layer between two glass plates. The filling system includes a filling manifold which is brought into abutment with the bottom edges of the glass plates. A rubber gasket provides a seal between the manifold and the cassette, The gasket includes a trough extending along the bottom edge of the cassette which communicates with an opening adapted to receive an injector. Liquid gel material in the injector fills the cassette from the bottom to the top.

19 Claims, 5 Drawing Sheets

ELECTROPHORESIS CASSETTE SYSTEM WITH APPARATUS AND METHOD FOR FILLING SAME

This application is a continuation-in-part of Ser. No. 127,655 filed Dec. 2, 1987, now U.S. Pat. No. 4,929,329, which is a continuation-in-part of Ser. No. 043,212 filed Apr. 27, 1987, now abandoned.

FIELD OF THE INVENTION

The present invention is related to electrophoresis systems, and in particular to an improved method and apparatus for filling an electrophoresis cassette with gel.

BACKGROUND OF THE INVENTION

Proteins and other large biological molecules, including DNA, may be separated for analysis using electrophoresis techniques. One particularly important application of these techniques is the sequencing of the DNA and RNA molecules. In performing an electrophoresis separation of such molecules, a gel is formed between two non-conducting plates, such as glass, to form a thin sheet of gel between the glass surfaces. The surfaces at either end of the gel are each connected to a buffer reservoir which serve as electrodes. A potential is applied across the gel by connecting each reservoir to opposite polarities of a voltage source. The electrophoresis gel layer is typically formed between two glass plates in an electrophoresis cassette. Exemplary cassettes are shown in U.S. Pat. No. 4,576,693 and U.K. Patent Application 2,180,941A.

It is extremely important during the assembly of such cassettes that all dirt and other foreign objects be kept out of the gel layer and that the gel layer be uniform and bubble free. To assemble an electrophoresis cassette and fill it with gel material typically requires substantial training and practice on the part of a technician. In particular, filling the cassette with the electrophoresis gel requires skill and considerable time. The present invention is directed at apparatus for filling a gel cassette.

SUMMARY OF THE INVENTION

The present invention includes apparatus for filling a gel cassette of the type having front and back glass plates with gel therebetween. A filling manifold receives gel from an injector and distributes it along the width of the opening between the plates at the bottom edge of the cassette. A resilient seal includes a trough therein which is wider than the gap between the cassette plates. Gel is injected from an injector, such a syringe, through passages communicating with the trough to fill the cassette from the bottom.

Two embodiments are disclosed for the filling apparatus. In a first embodiment, the filling manifold is positioned by means of a fixture which holds the cassette and which brings the manifold into position against the bottom edge thereof. In a second embodiment, alignment posts are integrally mounted to the cassette and serve to hold the filling manifold in place while the liquid gel material is injected. The alignment posts may also be used to position an alignment bar for precise location of the cassette top plate during cassette assembly.

DESCRIPTION OF THE DRAWINGS

The advantages and operation of the present invention will become more clear upon the reading the following description of exemplary embodiments of the invention in conjunction with the accompanying drawings of which.

DESCRIPTION OF THE PREFERRED EMBODIMENT

Figure 1:
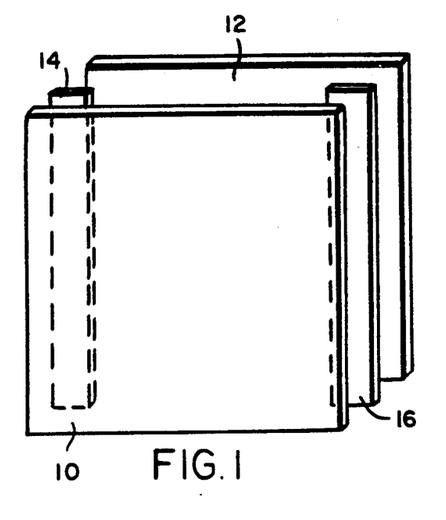
FIGS. 1-5 illustrate the construction and assembly of a typical electrophoresis cassette with which the invention may be used.

Referring to FIGS. 1-4, there is shown a typical gel cassette used for electrophoresis separation. Referring to FIG. 1, two flat plates 10 and 12 are brought together facing one another and separated by side spacers 14 and 16. The front and back plates should be made of a flat, non porous insulator which does not react with the gel material or the molecules being analyzed. Typically, plates 10 and 12 are formed of glass. Front and back plates are typically on the order of 8 inches by 12 inches.

Separators 14 and 16 are placed between the front and back plates 10 and 12 when they are assembled to form a uniform gap between the plates in which the gel is placed. The spacers determine the gel thickness and are on the order of 0.010 to 0.020 inches thick. Spacers 14 and 16 are on order of ⅜" wide and are typically formed from a sheet of mylar or other suitable material.

Figure 5:
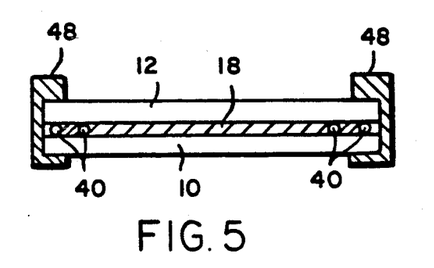

In place of flat spacers 14 and 16, monofilament separators may be used between plates 10 and 12, as shown in FIG. 5. In this cassette, two pieces of monofilament 40 are run down each side of the electrophoresis cassette to provide line contact seals. See the description of this cassette in the parent to this application, Ser. No. 127,655, also described in published U.K. patent application 2,206,696A.

Figure 2:
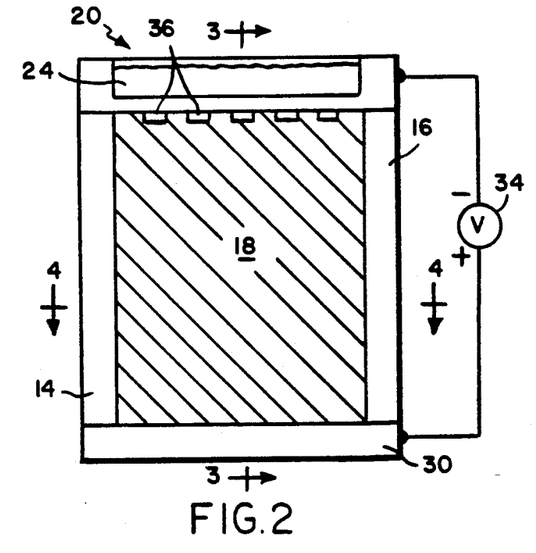
Figure 3:
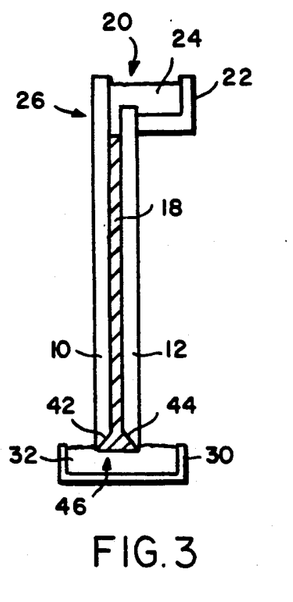
Figure 4:
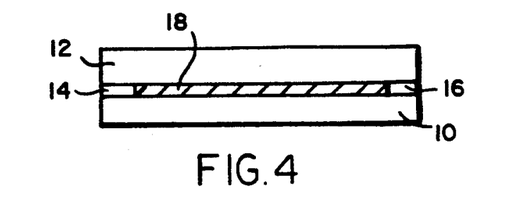

A reservoir 20 containing a buffer solution 24 is formed at the top of the cassette to provide an electrical connection to the top of the gel material 18. Typically, the reservoir is formed between an upper extension 26 of the front glass plate 10 and a rear piece 22 which forms the floor and sides of the rear of the reservoir. One or both of the bottom edges of plates 10 and 12 may have bevels 42 and 44 facing the gel layer 18. This provides a lower resistance along the bottom edge of the gel and reduces non-uniformities in the electric field which may be caused by unevenness in the bottom edge of the gel layer.

The bottom of the gel cassette is immersed in a bottom reservoir 30 containing a second buffer solution 32 which provides electrical contact with the bottom of the gel layer 18. A voltage source 34 is electrically connected between the top buffer solution 24 and the bottom buffer solution 32. Typically, the voltage from voltage source 34 is on the order of 1000 volts. The electric potential between the top and bottom buffer solutions induces an electric field within the gel layer 18. The objective is to provide a completely uniform electric field within the gel layer 18 having equipotential lines which are exactly parallel to the horizontal extent of the gel layer. In FIG. 2, a plurality of wells 36 are formed in the top of the gel layer 18. A collection of molecules to be separated is injected into each of the wells by means of a hypodermic needle small enough to fit in the narrow opening between the front and back plates 10 and 12 of the gel cassette.

Figures 6, 7A, 7B, 8:
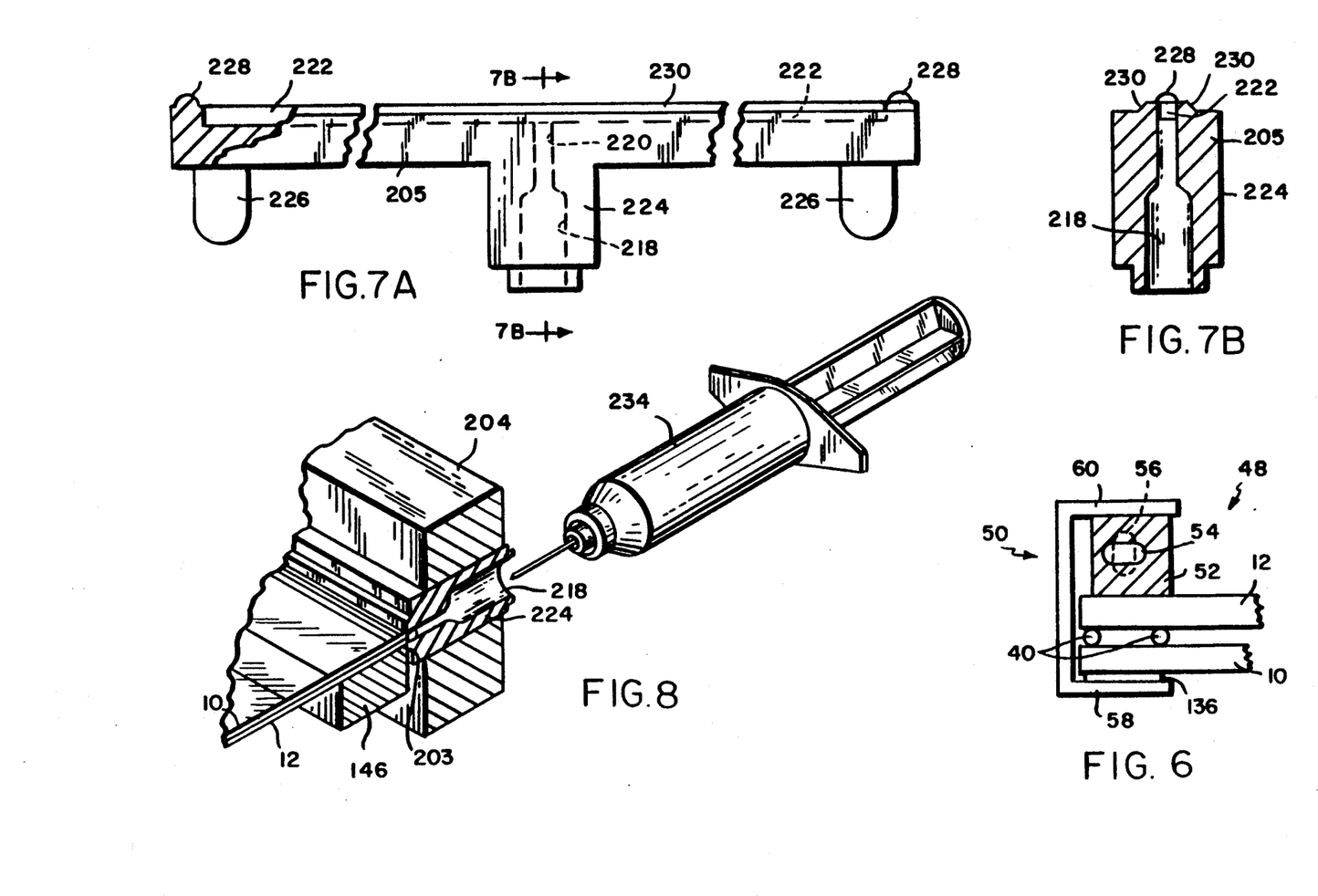
FIG. 6 shows the side clamps for the cassette.
FIGS. 7A and 7B show the cassette filling manifold sealing gasket.
FIG. 8 shows the filling manifold and gasket in place against the cassette and ready to receive liquid gel from an injector.

Side clamps 48 are used to hold the front and back plates 10 and 12 in contact with the spacers. These clamps run the entire length of the gel cell from the bottom to the top of plates 10 and 12. Referring to FIG. 6, a clamp support piece 50 is formed from a channel shaped piece of material, typically a machined or molded piece of plastic such as ABS or urethane, which runs the entire length of the gel cassette. A first side 58 of the channel bears against the front face of glass plate 10 through a plastic shim strip 136. A rubber locking piece 52 bears against the opposite face of the gel cassette on glass plate 12. The rubber piece 52 has a square outside configuration and also runs the length of the gel cassette. Rubber piece 52 is held against the back face of the cassette by the second side 60 of the channel piece 50.

An oval shaped opening 54 is formed in the rubber piece 52 and goes through the length thereof. The longer dimension of opening 54 is parallel to the back face of glass plate 50. To clamp the gel cassette together, a solid, oval-shaped tensioning rod is put into hole 54 for the entire length of the rubber piece. The rod is then twisted 90 degrees until it has the orientation shown by dotted lines 56 in FIG. 6. In this manner, a uniform pressure may be quickly and easily applied to the front and back plates 10 and 12 across the locations of monofilament spacers 40.

To form the gel layer, the components in FIG. 1 are brought together as described above. The front and back glass plates 10 and 12 are spaced apart by the spacers 14 and 16 or by monofilament separators 40. The edges of front and back plates 10 and 12 are clamped together so that the gel material which will be inserted between the plates cannot escape through the sides.

Prior to the present invention, a strip of tape was usually placed along the bottom of the gel cell to provide a seal. A suitable material such as a polyacrylamide or agarose gel is then used to fill the space between plates 10 and 12. These materials are liquid when they are poured or injected between the plates, after which the materials solidify to form a gel. It is essential for the proper operation of the electrophoresis separation that the gel be absolutely uniform. Any imperfection in the gel will affect the speed and direction of the molecules' diffusion under the influence of the electric field applied to the gel. Imperfections may be caused by air bubbles or dust within the gel or by other factors, as discussed below.

Current methods of filling gel cassettes such as shown in FIGS. 1–6 require considerable training and skill in order to produce an acceptable gel layer having uniform thickness and no discontinuities, such as would result from bubbles or dust particles in the gel layer. The method described below of injecting gel into the cassette results in a more uniform thickness in the gel layer, compared with prior art methods, resulting in enhanced performance and accuracy.

Figure 9:
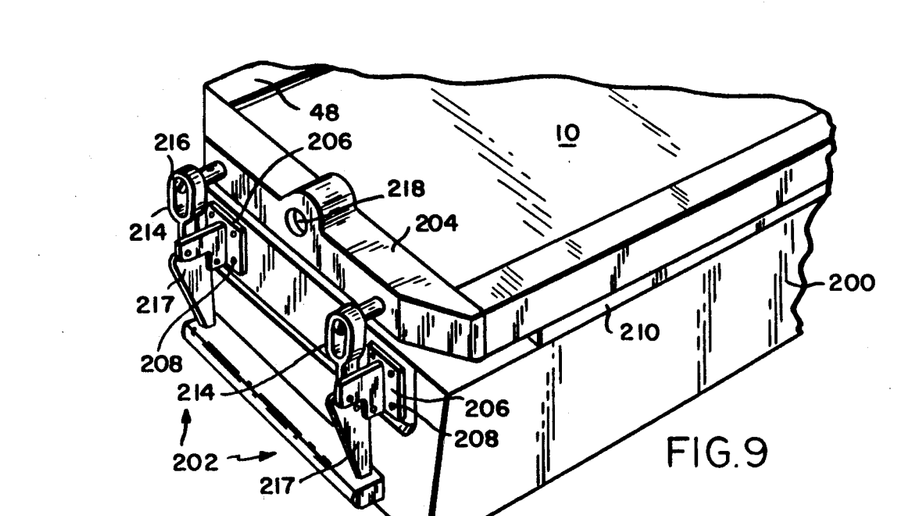
FIGS. 9-11 illustrate a filling apparatus in which the filling manifold is held in place against a cassette by means of an external clamping mechanism.
Figure 10:
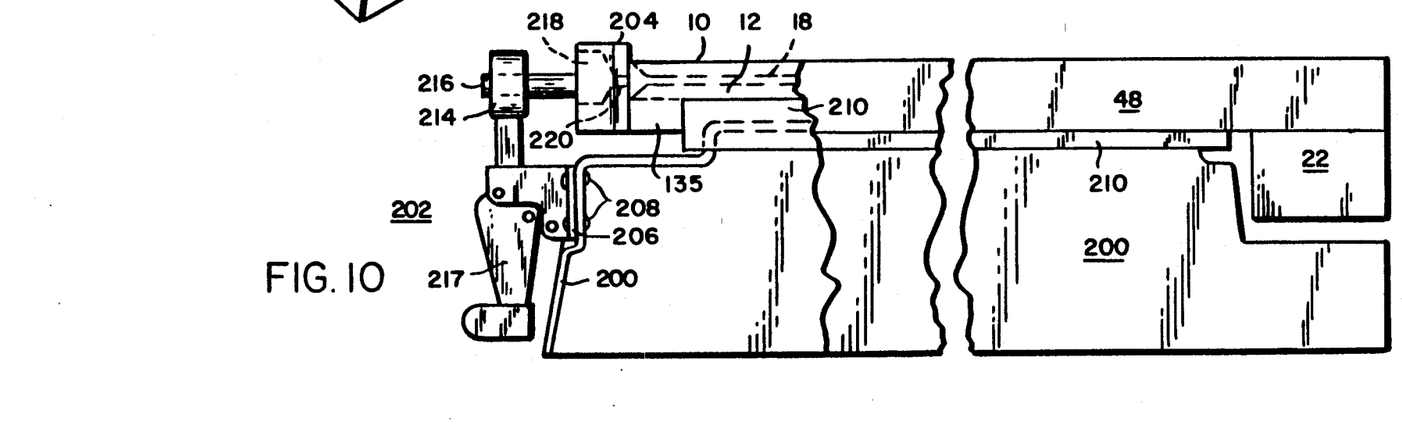

Referring to FIG. 9 an apparatus is shown in perspective view for injecting gel into the novel cassette described above. FIG. 10 is a side view of the apparatus with certain sections exposed in a cut-away portion.

The filling apparatus includes a base 200 which serves to support the cassette in a horizontal position as described in more detail below. A mechanism, shown generally at 202, is provided to position and clamp to the bottom of the gel cassette a filling manifold 204. Referring to FIG. 8, manifold 204 includes a rigid support bar 203 into which a resilient rubber sealing gasket 205 is inserted. Gasket 205 is shown in FIGS. 7A and 7B and described in more detail below. Manifold 204 serves to seal the bottom of the cassette while it is being filled with gel and also provides a passage way or manifold through which gel is injected into the space between the front and tack glass plates of the cassette.

Base 200 may be made from aluminum or other suitable material. The clamping mechanism 202 is attached to base 200 by means of bolts 208 which pass through holes in mounting plates 206 of the clamping mechanism and which screw into corresponding threaded holes or nuts in base 200. The holes in mounting plates 206 are slightly oversized so that the position of the clamping mechanism may be adjusted slightly.

A flat, rigid plate 210 is mounted on top of base 200. A lateral block piece 135 may be attached to the bottom edge of the back plate 12 to provide a stop which abuts against the front edge of plate 210. When in position to be filled, as shown in FIGS. 9 and 10, the cassette has its back plate 12 resting on support plate 210. It is important that the top surface of support plate 210 be flat and horizontal.

Figure 11:
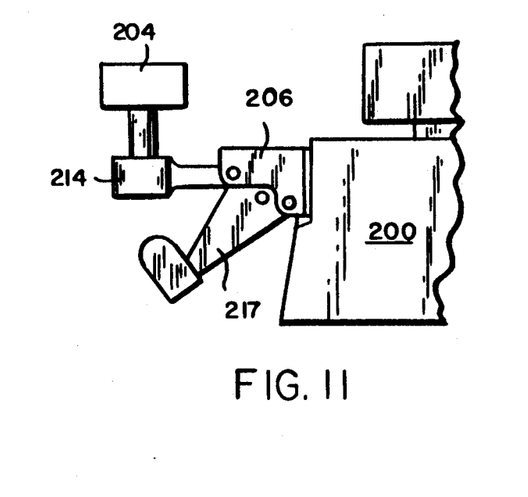

Clamping mechanism 202 includes right and left pivoting support pieces 214 which are attached to the rigid manifold support bar 203, such as by screws 216 or other means. In operation, support piece 214 and manifold block 204 are pivoted out of the way, as shown in FIG. 11, to allow the gel cassette to be placed in position as shown in FIG. 10. Following that, the manifold block is moved into place against the edge of the gel cassette, and is held in place by means of locking cams 217. The dimensions of clamping mechanism 202 and manifold 204 are such that sufficient force is applied by the clamping mechanism to insure a gel tight seal between the rubber insert 205 in manifold 204 and bottom edges of the front and back plates of the cassette. No more force than is necessary should be applied to avoid possible deformation of the cassette.

Manifold 204 includes a large opening 218 in the side opposite the gel cassette. This opening is designed to fit an injector, such as syringe 234 shown in FIG. 8, for injecting gel medium between the front and back plates of the cassette.

The rubber insert 205 of rigid manifold block 204 should be stiff enough to ensure that a secure contact is maintained between itself and the bottom edge of the gel cassette along its length, and should also be resilient enough to provide a seal which will not allow gel material or air to pass. Silastic rubber is used for insert 205 in the described embodiment. A positive locking mechanism between the injector and the manifold may be provided, such as luer fitting.

The configuration of the rubber gasket insert 205 is shown in more detail in FIGS. 7A, 7B, and 8. FIG. 7A is a top view of the insert removed from the filling manifold 204. FIG. 7B is a side view through the rubber insert taken at the location indicated in FIG. 7A. FIG. 8 shows the insert and manifold in place against the bottom edges of plates 10 and 12 ready to receive liquid gel from injector 234.

A groove 222 extends across the width of insert 205. This groove communicates with a narrow opening 220 which in turn communicates with a larger opening 218 adapted to receive the syringe injector 234. In the preferred embodiment, the width of groove 222 is approximately 0.06 inches wide, or approximately six times the plate separation. Groove 222 is approximately 0.06 inches deep.

Groove 222 faces the opening at the bottom edge of the cassette between plates 10 and 12. When liquid gel material is injected by syringe 234, it passes through opening 220 into groove 222, and from there into the volume between the cassette plates. Two bosses 228 protrude from the rubber insert on either side of groove 222 to provide a positive seal at each end of the groove. When used with a cassette having the monofilament spacers shown in FIG. 5, bosses 228 should abut the outermost monofilament spacer on each side to insure a positive seal. Two ribs 230 protrude slightly forward on either side of groove 222 and serve to provide a positive seal between rubber insert 205 and the edges of top and bottom plates 10 and 12.

Preferably, rubber insert 205 is removable from the filling manifold 204. This allows the insert to be easily cleaned and to be replaced if necessary. Two alignment knobs 226 may be provided on rubber insert 205. Alignment knobs 226 fit tightly in corresponding holes in manifold 204, not shown, and serve to ensure that the ends of the rubber insert stay in place in the filling manifold.

To assemble and fill a cassette, the following steps should be carried out. First, the front and rear plates should be cleaned and optionally silanized thoroughly. The monofilament side spacers are then cleaned and assembled to the top plate 10. Next, the bottom plate assembly with the reservoir attached is positioned on the filling apparatus, being aligned by the aluminum plate 210. Next, dust should be removed from both the top and bottom plates, and the top plate immediately assembled to the bottom plate with the bottom edge of the top plate slightly above the bottom edge of the rear plate. The side clamps 48 are then put into place without tightening the locking rods.

Next, manifold 204 is moved into place against bottom plate 12 and locked into place with locking cam 217. If necessary, a small amount of grease may be put onto the front face of gasket 205 to aid in providing a good seal. This is typically only necessary along the outside edges of the seal. The front plate 10 is then slowly moved downward until it just touches the rubber insert 205 of manifold 204 to provide a seal, and the locking rods of side clamps 48 are twisted into the locked position.

A syringe is then filled with liquid gel solution, being careful to remove all air bubbles from the syringe. In the described embodiment, a 30 cc syringe is used. The syringe is then inserted into its receptacle 218 in manifold 204. The syringe plunger is slowly depressed to fill the cassette until the gel solution overflows the cassette at the top. The gel material, although liquid, has sufficient surface tension to fill up the entire area between the front and back glass plates without gaps as the syringe plunger is depressed. After the cassette has been completely filled, a comb with the desired well configuration is inserted into the top of the gel material. If necessary, the plunger is depressed further until the channels at either side of the cassette between the monofilament spacers are completely filled. After the cassette has been completely filled, the filler block is swung out of the way to remove pressure on the plates. The gel is allowed to polymerize to a solid before the cassette is removed from the filling fixture, and in particular before the cassette is moved from its horizontal position.

Figures 14, 15:
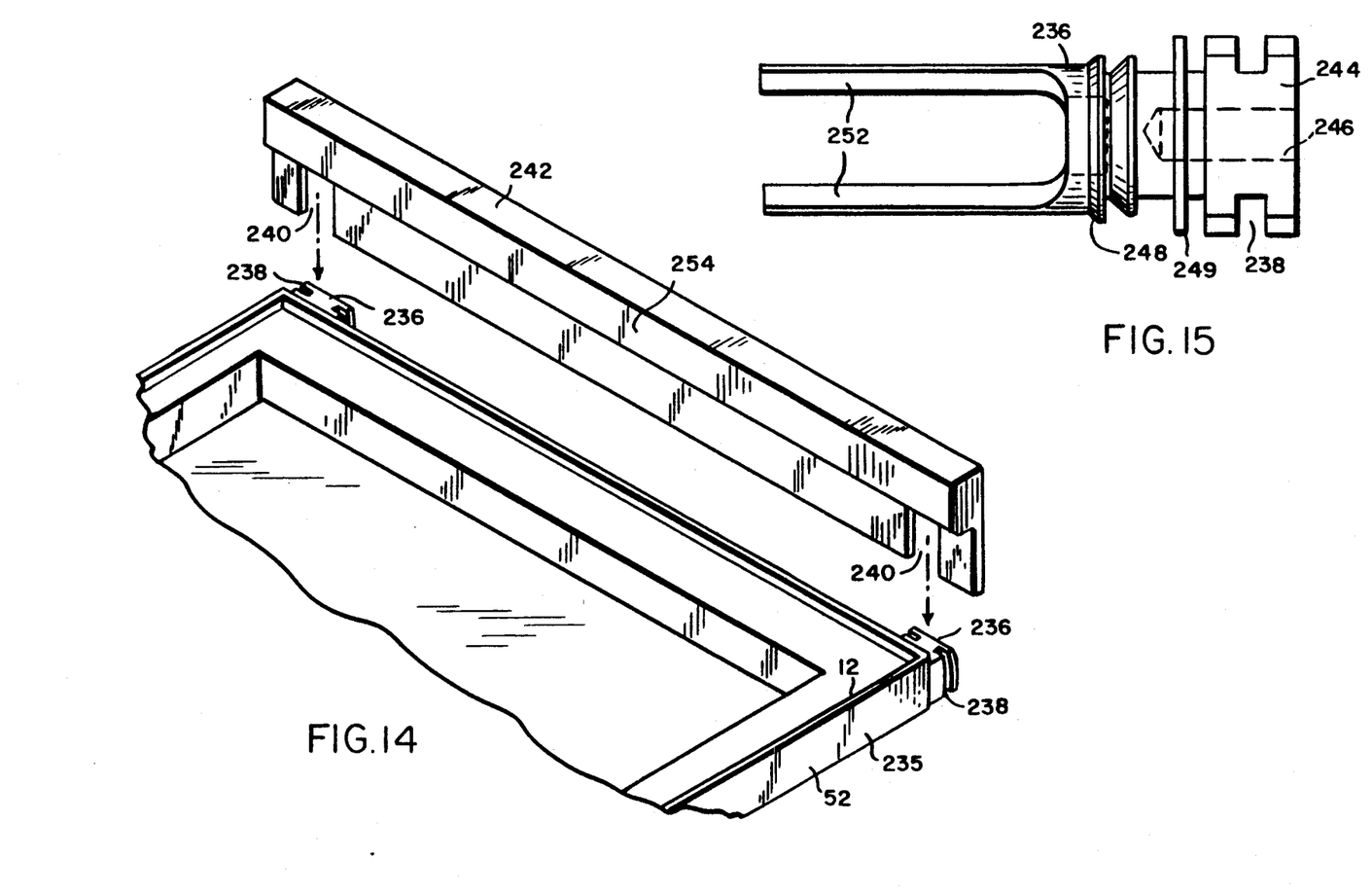
FIG. 14 shows an alignment bar which may be used to accurately locate the front plate of a cassette.
FIG. 15 shows details of the alignment post.

FIGS. 12-15 illustrate an alternate mechanism for filling an electrophoresis cassette. Referring to FIG. 14, the lower portion of back plate 12 is shown. A rubber frame section 235 is attached to the outside of bottom plate 12, such as by an adhesive. Two alignment posts 236 are mounted in rubber frame 235. Each of the alignment posts 236 has grooves 238 formed therein on the sides which are adapted to allow corresponding slots 240 in an alignment bar 242 to be engaged therewith, as described below.

FIG. 15 is a drawing showing more details of alignment posts 236. Slot 238 is formed in an enlarged portion 244 of the post 236. The left hand portion of the post includes two legs 252 which extend within rubber frame section 235. The oval rods used to provide the clamping pressure, discussed above in connection with FIG. 6, run inside the rubber frame 235. Legs 252 of the alignment post are sufficiently spaced apart so that the oval rod may run between them and into an opening 254 in the end of the post. Two retention rings 248 are formed in post 236 and serve to retain the post within the resilient rubber frame 235. An abutment plate 249 is formed next to section 244 which buts up against the rubber frame 235 and serves to ensure that the alignment slot 238 is precisely positioned with respect to the end of the frame 235 and attached glass plate 12. Thus, both slots 238 and the end surface 246 of post 236 are precisely located with respect to the bottom edge of plate 12.

The alignment bar 242 may be accurately located at the bottom end of the cassette by engaging corresponding slots 240 into slots 238 of alignment posts 236. Alignment bar 242 is dimensioned so that one face 254 abuts the bottom edge of glass plate 12 and extends upwardly therefrom when the alignment bar is engaged in slots 238. This allows top plate 10 to be positioned very precisely with respect to the bottom plate 12 by moving it downwardly with respect to bottom plate 12 until its bottom edge connects face 254 of the alignment bar. At this point, side clamps 48 are positioned along the edges of the cassette and the clamping force is applied.

Figures 12, 13:
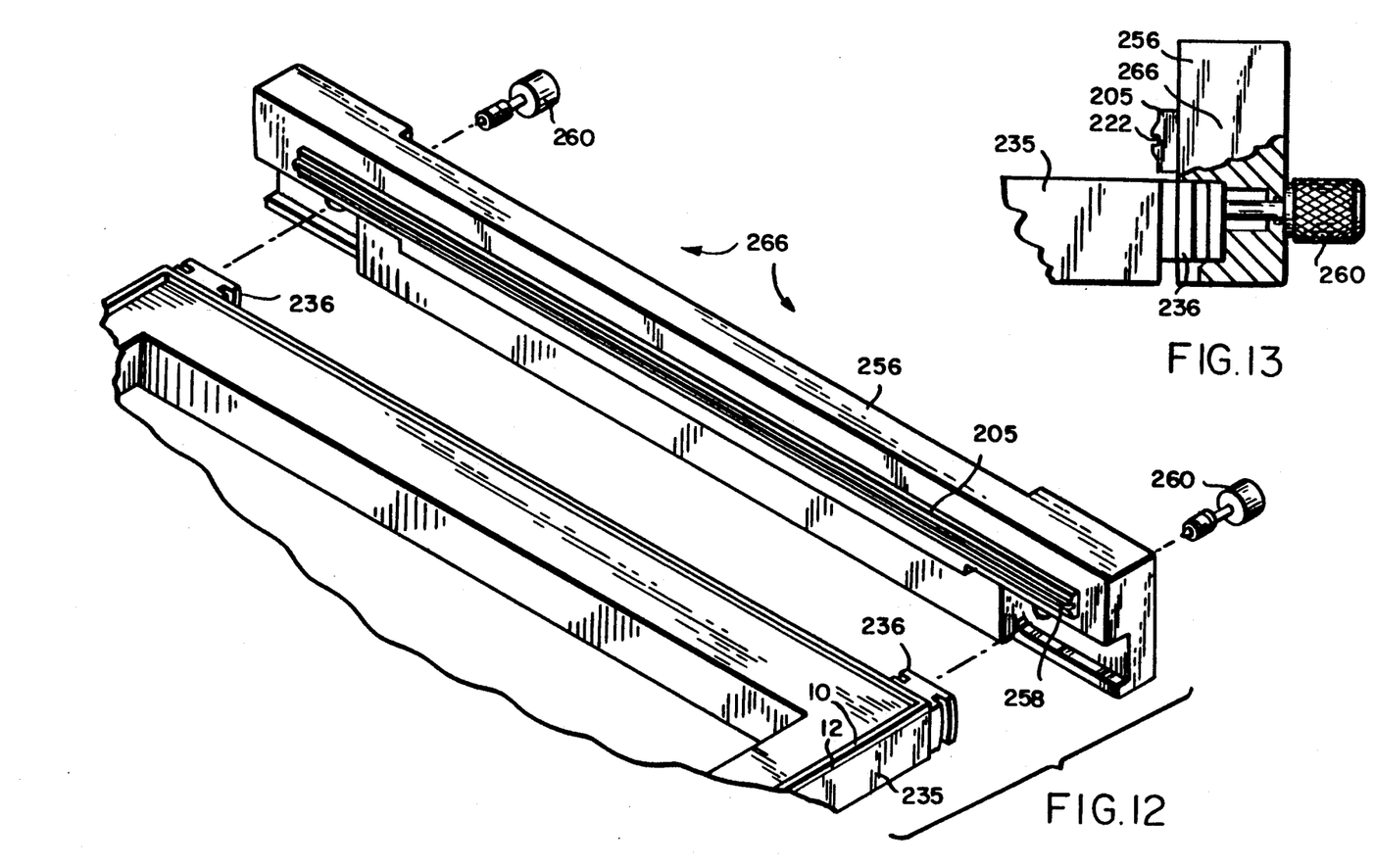
FIGS. 12 and 13 show a filling mechanism in which the filling manifold is held against the cassette by means of integral alignment posts.

After the top and bottom plates have been aligned and clamped in place, a filling manifold 266 is place over alignment posts 236. Manifold 266 includes a rigid support portion 256 and a rubber insert 205 similar to that described above and shown in FIGS. 7A and 7B. Two recesses 258 are formed in the bottom portion of support 256 as shown in FIG. 12. The back surfaces of recesses 258 abut the end surfaces 246 of alignment posts 236 to position the opening in the rubber insert 205 so that it is accurately located opposite the space between the cassette plates. Manifold 266 is then secured to the cassette, for example by means of knurled screws 260 which extend through holes in the support 256 and engage a threaded hole 246 in alignment post 236. This allows a very accurate "preload" force to be applied to the ribs 230 on either side of groove 222. In the described embodiment the compression of ribs 230 is approximately 0.025 inches. Bottom plate 12 of the cassette should be supported by a flat, horizontal surface, not shown, which supports back plate 12 over substantially all of its area.

The filling manifold shown in FIGS. 12 and 13 is capable of aligning the filling manifold more precisely than the mechanism shown in FIGS. 9-11. The end surfaces 246 of alignment post 236 provide closer tolerances by abutting against the corresponding back surfaces of recesses 258 than does the locking mechanism 202 described above. Due to the improved alignment, lower forces are necessary to ensure a seal between rubber insert 205 and the bottom edges of plates 10 and 12, which reduces the tendency of front and back plates to distort. Alignment bar 242 and manifold support 256 may be fabricated as a single structure, such as by forming appropriate alignment slots 240 on the backside of manifold 256. This reduces the number of individual pieces needed to assemble and fill a cassette. After manifold 256 has been positioned, liquid gel material is injected into the area between the cassette plates as described above.

The use of the described system for filling a gel cassette has many advantages over prior art methods. First, it is easier to maintain a smooth bottom surface on the gel than when a cassette is filled from the top with the bottom taped as has been previously done. Second, an operator may carefully watch the gel material filling the gel cassette as it is being injected. Air bubbles, dust particles, or other causes of imperfections in the gel can be observed. If this occurs, the gel material may be pulled back into the syringe by pulling on the plunger, and the affected area may be refilled. This is particularly useful when air bubbles are formed, since these bubbles are frequently eliminated when the cassette is refilled.

Additionally, the procedure described above provides a gel layer 18 between front and back plates 10 and 12 which is more uniform in thickness than can be achieved by many prior art methods. Typically, gel cassettes of the type shown in FIG. 1 have been filled by sealing the bottom of an assembled gel cassette and pouring the gel material into the top of the cassette while the cassette is in a vertical or near vertical position. This procedure is much more prone to result in air bubbles and dust particles within the gel layer.

Filling a vertical cassette also results in a slight bulging outward of the front and back plates 10 and 12 due to hydrostatic pressure resulting from the weight of the gel material. This effect is more pronounced at the bottom of the gel cassette where the hydrostatic pressure is greatest. When using the filling method described, no such hydrostatic pressure is applied to the plate, since the cassette is filled in a horizontal position with substantially the entire surface of back plate 12 supported by a support.

Since the gel layer 18 will change from a liquid to a solid state after the gel cassette has been filled, little or no hydrostatic pressure is applied to front and back plates 10 and 12 by the solidified gel material when the cassette is moved to a vertical position. Because of this, back plate 12 can be made extremely thin, and may even be thinner than front plate 10, which must be thick enough to support its weight without bowing during the filling operation. Where radiometric detection methods are used, a thinner rear plate 12 may provide a smaller separation between the radio labelled molecules and the detectors.

In the preferred embodiment, front plate 10 is 3/16 inch thick and rear plate 12 is 1/16" thick. For a cassette with dimensions on the order of eight by twelve inches, a 3/16 inch thick front plate will bend a negligible amount under gravitational forces. The 1/16 inch front plate would bow out approximately one thousandth of an inch from the hydrostatic forces produced by conventional filling technique wherein the cassette is filled in a vertical position.

There has been described a novel system for filling an electrophoresis cassette which has advantages over methods and devices previously used. It should be apparent that modifications to the preferred embodiments disclosed herein will be made by those of ordinary skill when using the teachings of the present invention in different applications and situations. Accordingly, the invention should not be limited by the particular embodiments utilized above to explain the features of the invention by way of example. Rather, the invention should only be interpreted in accordance with the following claims.

What is claimed:

1. An electrophoresis cassette system comprising;
    an electrophoresis cassette of the type comprising cassette housing means having first and second parallel plates mounted therein in a mounted position and means for holding said plates separated by a predetermined distance, at least two sealing means, each for providing a seal between said plates along one side thereof, and defining openings at opposite longitudinal ends of said plates, said openings each having a depth equal to the space between the plates and a transverse width substantially equal to the transverse distance between said sealing means;
    alignment means mounted to said housing means;
    a support bar removably engagable with said alignment means to maintain said support bar in a predetermined spatial relationship to said housing;
    filler gasket means mounted to said support bar and comprising means for surrounding one of said openings and defining an interior for placement in registration with said opening, said filler gasket means and said support bar being dimensioned to seal said opening when said support bar is engaged with said alignment means; and
    an aperture extending through said support bar in registration with the interior of said filler gasket means.

2. The system of claim 1 further comprising syringe means for housing electrophoresis gel for dispensing into said cassette having a cylindrical output conduit for removable engagement with said aperture.

3. The system of claim 1 wherein said filler gasket means comprises parallel transversely extending elastomeric ribs, each for engagement with a longitudinal end of one plate and defining a trough therebetween.

4. The system according to claim 3 wherein said filler gasket means comprises first and second bosses, each for engaging said seal means at opposite transverse sides of said trough for sealing the interior of said filler gasket to said opening between said plates.

5. The system according to claim 1 wherein said alignment means comprises first and second transversely spaced posts each having a first end extending longitudinally therefrom and comprising stop means for determining the spacing of said support bar to said plates.

6. The system according to claim 5 wherein said support bar comprises a face having recesses each for receiving one of said posts and wherein said filler gasket is mounted to said face.

7. The system according to claim 6 further comprising threaded fastening means for extending through said support bar and wherein each of said posts includes a threaded aperture adapted to receive said threaded fastening means to maintain said filler gasket in sealing engagement with said plates.

8. The system according to claim 1 wherein said support bar is formed to be reversible with respect the first position by means of rotation about a transverse axis and engageable with said housing as an element to align said plates prior to fixing of said plates in said mounted position.

9. The system according to claim 4 wherein said alignment means comprises first and second transversely spaced posts each having a first end received in said housing and a second end extending longitudinally therefrom and comprising stop means for determining the spacing of said support bar to said plates.

10. The system according to claim 9 wherein said support bar comprises a face having recesses each for receiving one of said posts and wherein said filler gasket is mounted to said face.

11. The system according to claim 10 further comprising threaded fastening means for extending through said support bar and being received in a threaded apertures in said posts for maintaining said filler gasket in sealing engagement with said plates.

12. The system according to claim 11 wherein said support bar is formed to be reversible with respect to the first position by means of rotation about a transverse axis and engageable with said housing as an element to align said plates prior to mounting of said plates in said mounted position.

13. A filler for an electrophoresis cassette comprising:
a support bar for removable engagement mounting to an electrophoresis cassette housing means of the type having first and second parallel plates mounted therein and means for holding said plates separated by a predetermined distance, seal means each providing a seal between said plates adjacent opposite transverse sides of said plates and said housing, and defining openings at opposite longitudinal ends of said plates, said openings each having a depth equal to the space between the plates and a transverse width equal to the transverse distance between sealing means;
filler gasket means mounted to said support bar and comprising means for surrounding one said opening and defining an interior for placement in registration with said opening, said filler gasket means and said support bar being dimensioned to seal said opening when said support bar is engaged with said alignment means; and
an aperture extending through said support bar in registration with the interior of said filler gasket means.

14. Apparatus for injecting gel into an electrophoresis cassette of the type having first and second parallel plates separated by spacers along two sides thereof to form a thin gel cavity between the plates bounded on the sides by said spacers and open on the top and bottom edges of the cassette, the cavity adapted for being filled with said gel, the injecting apparatus including:
injection means, having a nozzle, for containing a quantity of gel and for injecting the gel out through the nozzle;
a filling manifold, including:
gasket means for sealing the bottom opening of the gel cavity by being pressed against the bottom edge of the cassette, the gasket means being formed of a resilient material and including means for receiving the injection means nozzle and for conveying gel from said nozzle to the bottom edge of the gel cavity when pressed against the cassette bottom edge; and
rigid support means for holding the gasket means; and
positioning means for holding the filling manifold in a position with the gasket means against the bottom of the cassette and for maintaining the filling manifold in said position with sufficient force to seal the interface between the gasket means and the cassette bottom edge to prevent leakage of gel.

15. The apparatus of claim 14 wherein the gasket means includes a groove which is wider than the separation between the first and second plates of the cassette and which is located abutting and in alignment with the bottom opening of said cassette when the filling manifold is in said position.

16. The apparatus of claim 15 wherein the positioning means includes:
clamp means for selectively moving the filling manifold into a first position against the bottom of the cassette and for maintaining the filling manifold in said first position;
a base for supporting the cassette while gel is injected, including a flat, substantially horizontal surface adapted to support one of said plates;
means for attaching the clamp means to the base;
the clamp means being adapted to allow the filling means to be moved from said first position to a second position to allow a cassette to be placed on and removed from said support means without interference from the filling manifold.

17. The apparatus of claim 15 wherein the positioning means includes:
first and second transversely spaced alignment posts attached to and in fixed alignment with the first plate of the cassette; and
wherein the support means includes two receiving means, each adapted to receive one of said alignment posts, for positioning the support means with respect to the first plate.

18. The apparatus of claim 17 further comprising an alignment bar adapted to mate with said alignment posts so as to be held in a fixed position thereby, the alignment bar including a face against which the second of the plates may be placed to align the second plate with the first plate when the alignment bar is in position.

19. The apparatus of claim 18 wherein said alignment bar is formed as a part of the filling manifold support means.

* * * * *